United States Patent
Kita et al.

(10) Patent No.: US 10,702,507 B2
(45) Date of Patent: Jul. 7, 2020

(54) ENDOPARASITE CONTROL AGENT

(71) Applicants: THE UNIVERSITY OF TOKYO, Tokyo (JP); NIHON NOHYAKU CO., LTD., Tokyo (JP)

(72) Inventors: Kiyoshi Kita, Tokyo (JP); Akiyuki Suwa, Osaka (JP); Masatsugu Oda, Osaka (JP)

(73) Assignees: THE UNIVERSITY OF TOKYO, Tokyo (JP); NIHON NOHYAKU CO., LTD., Tokyo (JP)

( * ) Notice: Subject to any disclaimer, the term of this patent is extended or adjusted under 35 U.S.C. 154(b) by 210 days.

(21) Appl. No.: 16/159,882

(22) Filed: Oct. 15, 2018

(65) Prior Publication Data

US 2019/0046511 A1    Feb. 14, 2019

Related U.S. Application Data

(62) Division of application No. 15/120,765, filed as application No. PCT/JP2015/056326 on Mar. 4, 2015, now abandoned.

(30) Foreign Application Priority Data

Mar. 5, 2014 (JP) ................. 2014-042876

(51) Int. Cl.
| | |
|---|---|
| A61K 31/44 | (2006.01) |
| A61K 31/166 | (2006.01) |
| C07D 213/643 | (2006.01) |
| C07D 213/61 | (2006.01) |
| C07D 215/227 | (2006.01) |
| C07D 277/68 | (2006.01) |
| C07D 231/20 | (2006.01) |
| C07D 233/66 | (2006.01) |
| C07D 241/44 | (2006.01) |
| C07D 239/60 | (2006.01) |
| C07D 239/34 | (2006.01) |
| C07D 263/58 | (2006.01) |
| C07D 241/18 | (2006.01) |
| C07C 233/66 | (2006.01) |
| C07C 233/73 | (2006.01) |

(52) U.S. Cl.
CPC ............ *A61K 31/44* (2013.01); *A61K 31/166* (2013.01); *C07C 233/66* (2013.01); *C07C 233/73* (2013.01); *C07D 213/61* (2013.01); *C07D 213/643* (2013.01); *C07D 215/227* (2013.01); *C07D 231/20* (2013.01); *C07D 239/34* (2013.01); *C07D 239/60* (2013.01); *C07D 241/18* (2013.01); *C07D 241/44* (2013.01); *C07D 263/58* (2013.01); *C07D 277/68* (2013.01)

(58) Field of Classification Search
None
See application file for complete search history.

(56) References Cited

U.S. PATENT DOCUMENTS

| | | | |
|---|---|---|---|
| 4,093,743 A | 6/1978 | Yabutani et al. | |
| 4,957,533 A | 9/1990 | Arnold et al. | |
| 2009/0156682 A1 | 6/2009 | Mansfield et al. | |
| 2009/0318290 A1 | 12/2009 | Coqueron et al. | |
| 2010/0048647 A1 | 2/2010 | Suwa | |
| 2010/0063155 A1 | 3/2010 | Coqueron et al. | |
| 2010/0087494 A1 | 4/2010 | Coqueron et al. | |
| 2010/0292239 A1 | 11/2010 | Stierli et al. | |
| 2011/0092558 A1 | 4/2011 | Stierli et al. | |
| 2011/0136831 A1 | 6/2011 | Oda et al. | |
| 2011/0237678 A1 | 9/2011 | Mansfield et al. | |
| 2014/0088157 A1 | 3/2014 | Kita et al. | |
| 2014/0296066 A1 | 10/2014 | Pitterna et al. | |
| 2015/0232424 A1 | 8/2015 | Pitterna et al. | |
| 2015/0259322 A1 | 9/2015 | Kita et al. | |

FOREIGN PATENT DOCUMENTS

| | | |
|---|---|---|
| JP | 53-9739 | 1/1978 |
| JP | 1-151546 | 6/1989 |
| WO | 2007/060162 | 5/2007 |
| WO | 2007/108483 | 9/2007 |

(Continued)

OTHER PUBLICATIONS

International Search Report dated Apr. 14, 2015 in International Application No. PCT/JP2015/056326.

(Continued)

*Primary Examiner* — Dennis Heyer
(74) *Attorney, Agent, or Firm* — Wenderoth, Lind & Ponack, L.L.P.

(57) ABSTRACT

The present invention is intended to provide a novel parasiticide, antiprotozoal or other endoparasite control agents which are effective for controlling animal endoparasites that have been impossible to control by conventional ones. Provided is an endoparasite control agent comprising, as an active ingredient, a carboxamide derivative represented by the general formula (I):

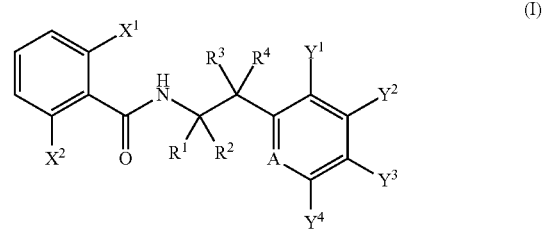

or a salt thereof.

7 Claims, No Drawings

(56) References Cited

FOREIGN PATENT DOCUMENTS

| WO | 2008/003745 | 1/2008 |
|---|---|---|
| WO | 2008/003746 | 1/2008 |
| WO | 2008/101975 | 8/2008 |
| WO | 2008/101976 | 8/2008 |
| WO | 2008/126922 | 10/2008 |
| WO | 2009/009041 | 1/2009 |
| WO | 2009/012998 | 1/2009 |
| WO | 2009/127718 | 10/2009 |
| WO | 2010/106071 | 9/2010 |
| WO | 2012/118139 | 9/2012 |
| WO | 2013/064519 | 5/2013 |
| WO | 2014/034751 | 3/2014 |
| WO | 2014/177582 | 11/2014 |
| WO | 2015/028427 | 3/2015 |
| WO | 2015/055535 | 4/2015 |
| WO | 2015/078800 | 6/2015 |

OTHER PUBLICATIONS

Kiyoshi Kita, "New strategy for antiparasitic drug development", Infection, Inflammation & Immunity, vol. 40, No. 4, pp. 310-319, Jan. 20, 2011, with English translation.
International Preliminary Report on Patentability dated Sep. 6, 2016 in International Application No. PCT/JP2015/056326.
Extended European Search Report dated Sep. 7, 2017 in European Application No. 15758724.7.

ENDOPARASITE CONTROL AGENT

TECHNICAL FIELD

The present invention relates an endoparasite control agent comprising a carboxamide derivative or a salt thereof as an active ingredient, and a method for controlling endoparasites, comprising orally or parenterally administering the endoparasite control agent.

BACKGROUND ART

Certain kinds of carboxamide derivatives have been known to have microbicidal activity (see Patent Literature 1 to 12). However, the literature does not describe that these compounds are effective for the disinfection or control of endoparasites in animals such as mammals and birds. It is also known that certain kinds of carboxamide derivatives are effective against nematodes that may damage agricultural products (see Patent Literature 4 or 5), but there is no specific disclosure as to whether these compounds are effective against endoparasites in animals. Furthermore, there is a report that compounds that inhibit succinate-ubiquinone reductase (mitochondrial complex II), which is one of the respiratory enzymes of endoparasites, can serve as an endoparasite control agent (see Non Patent Literature 1).

In addition, Patent Literature 13 discloses certain kinds of carboxamide derivatives which are effective against endoparasites. However, there is no disclosure of the effects of the compounds of the present invention against endoparasites.

Generally, parasitosis is caused by infestation of host animals with parasites such as unicellular protists (protozoa), multicellular helminths and arthropods. It is reported that the incidence of parasitosis in Japan has been remarkably decreased by improvement of environmental hygiene, but on a global scale, particularly in developing countries, parasitosis still widely prevails and causes tremendous damage. In recent years, there have been seen the introduction of infection sources via long- or short-term travelers having visited such countries; parasitic infection due to the consumption of food imports or raw meat and fish meat, which have become more available thanks to the advance in freezing and logistics technologies; and the transmission of parasitosis from pets. Under such circumstances, the incidence of parasitosis is on an upward trend again. Another problem is that immunodeficiency caused by mass administration of immunosuppressants, anticancer drugs, etc. or by AIDS etc. allows usually non-pathogenic or low-pathogenic parasites to express their pathogenicity and to cause opportunistic infection in hosts. Further, parasitosis in domestic animals, such as pigs, horses, cattle, sheep, dogs, cats and domestic fowls, is a universal and serious economic problem. That is, parasitic, infection of domestic animals causes anemia, malnutrition, debility, weight loss, and serious damage of intestinal tract walls, tissues and organs, and may result in decline in feed efficiency and productivity, leading to a great economic loss. Therefore, novel parasiticides, antiprotozoals or other endoparasite control agents have always been desired.

CITATION LIST

Patent Literature

Patent Literature 1: JP-A 01-151546
Patent Literature 2: WO 2007/060162
Patent Literature 3: JP-A 53-9739
Patent Literature 4: WO 2007/108483
Patent Literature 5: WO 2008/126922
Patent Literature 6: WO 2008/101975
Patent literature 7: WO 2008/101976
Patent literature 8: WO 2008/003745
Patent literature 9: WO 2008/003746
Patent literature 10: WO 2009/012998
Patent literature 11: WO 2009/127718
Patent literature 12: WO 2010/106071
Patent literature 13: WO 2012/118139

Non Patent Literature

Non Patent Literature 1: Kiyoshi Kita, "Kansen (Infection)", Winter 2010, Vol. 40-4, 310-319

SUMMARY OF INVENTION

Technical Problem

In view of the above-described circumstances, the present invention is mainly intended to provide a novel parasiticide, antiprotozoal or other endoparasite control agents which are effective for controlling animal endoparasites that have been impossible to control by conventional ones.

Solution to Problem

The present inventors conducted extensive research to solve the above-described problems. As a result, the present inventors found that a carboxamide derivative represented by the general formula (I) of the present invention and a salt thereof are highly effective for controlling endoparasites. The present inventors further conducted a great deal of examination and then completed the present invention. That is, the present invention relates to the following.

[1] An endoparasite control agent comprising, as an active ingredient, a carboxamide derivative represented by the general formula (I):

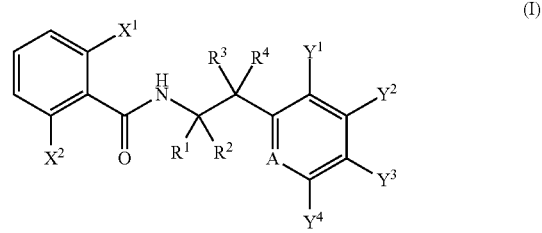

{wherein
A represents a nitrogen atom or a C—$Y^5$ group (wherein $Y^5$ is a hydrogen atom or a ($C_1$-$C_6$) alkyl group),
$X^1$ and $X^2$ may be the same or different and each represent
(a1) a hydrogen atom;
(a2) a halogen atom;
(a3) a ($C_1$-$C_6$) alkyl group;
(a4) a halo ($C_1$-$C_6$) alkyl group;
(a5) a ($C_1$-$C_6$) alkoxy group; or
(a6) a halo ($C_1$-$C_6$) alkoxy group,
$R^1$ and $R^2$ may be the same or different, and are selected from the group consisting of
(b1) a hydrogen atom;
(b2) a halogen atom;

(b3) a $(C_1\text{-}C_6)$ alkyl group;
(b4) a $(C_1\text{-}C_6)$ alkoxy group; and
(b5) a halo $(C_1\text{-}C_6)$ alkyl group, or optionally
(b6) $R^1$ and $R^2$ together with the carbon atom bound to $R^1$ and $R^2$ form a $(C_3\text{-}C_6)$ cycloalkane,
$R^3$ and $R^4$ may be the same or different, and are selected from the group consisting of
(c1) a hydrogen atom;
(c2) a halogen atom;
(c3) a $(C_1\text{-}C_6)$ alkyl group;
(c4) a $(C_1\text{-}C_6)$ alkoxy group; and
(c5) a halo $(C_1\text{-}C_6)$ alkyl group; or optionally
(c6) $R^3$ and $R^4$ together with the carbon atom bound to $R^3$ and $R^4$ form a $(C_3\text{-}C_6)$ cycloalkane,
$Y^1$ represents
(d1) a hydrogen atom;
(d2) a halogen atom;
(d3) a $(C_1\text{-}C_6)$ alkyl group;
(d4) a halo $(C_1\text{-}C_6)$ alkyl group;
(d5) a $(C_1\text{-}C_6)$ alkoxy group; or
(d6) a halo $(C_1\text{-}C_6)$ alkoxy group,
$Y^2$ and $Y^4$ may be the same or different, and each represent
(e1) a hydrogen atom;
(e2) a halogen atom;
(e3) a $(C_1\text{-}C_6)$ alkyl group;
(e4) a halo $(C_1\text{-}C_6)$ alkyl group;
(e5) a $(C_1\text{-}C_6)$ alkoxy group; or
(e6) a halo $(C_1\text{-}C_6)$ alkoxy group, and
$Y^3$ represents
(f1) a phenyl group;
(f2) a phenyl group having, on the ring, 1 to 5 substituting groups which may be the same or different and are selected from the group consisting of (a) a halogen atom, (b) a cyano group, (c) a nitro group, (d) a $(C_1\text{-}C_6)$ alkyl group, (e) a halo $(C_1\text{-}C_6)$ alkyl group, (f) a $(C_1\text{-}C_6)$ alkoxy group and (g) a halo $(C_1\text{-}C_6)$ alkoxy group;
(f3) a phenoxy group;
(f4) a phenoxy group having, on the ring, 1 to 5 substituting groups which may be the same or different and are selected from the group consisting of (a) a halogen atom, (b) a cyano group, (c) a nitro group, (d) a $(C_1\text{-}C_6)$ alkyl group, (f) a $(C_1\text{-}C_6)$ alkoxy group and (g) a halo $(C_1\text{-}C_6)$ alkoxy group;
(f5) a pyridyl group;
(f6) a pyridyl group having, on the ring, 1 to 4 substituting groups which may be the same or different and are selected from the group consisting of (a) a halogen atom, (b) a cyano group. (c) a nitro group, (d) a $(C_1\text{-}C_6)$ alkyl group, (e) a halo $(C_1\text{-}C_6)$ alkyl group, (f) a $(C_1\text{-}C_6)$ alkoxy group and (g) a halo $(C_1\text{-}C_6)$ alkoxy group;
(f7) a pyridyloxy group;
(f8) a pyridyloxy group having, on the ring, 1 to 4 substituting groups which may be the same or different and are selected from the group consisting of (a) a halogen atom, (b) a cyano group, (c) a nitro group, (d) a $(C_1\text{-}C_6)$ alkyl group, (e) a halo $(C_1\text{-}C_6)$ alkyl group, (f) a $(C_1\text{-}C_6)$ alkoxy group and (g) a halo $(C_1\text{-}C_6)$ alkoxy group;
(f9) a pyrimidyloxy group;
(f10) a pyrimidyloxy group having, on the ring, 1 to 3 substituting groups which may be the same or different and are selected from the group consisting of (a) a halogen atom, (b) a cyano group, (c) a nitro group, (d) a $(C_1\text{-}C_6)$ alkyl group, (e) a halo $(C_1\text{-}C_6)$ alkyl group, (f) a $(C_1\text{-}C_6)$ alkoxy group and (g) a halo $(C_1\text{-}C_6)$ alkoxy group;
(f11) a pyrazyloxy group;
(f12) a pyrazyloxy group having, on the ring, 1 to 3 substituting groups which may be the same or different and are selected from the group consisting of (a) a halogen atom, (b) a cyano group, (c) a nitro group, (d) a $(C_1\text{-}C_6)$ alkyl group, (e) a halo $(C_1\text{-}C_6)$ alkyl group, (f) a $(C_1\text{-}C_6)$ alkoxy group and (g) a halo $(C_1\text{-}C_6)$ alkoxy group;
(f13) a pyrazolyloxy group;
(f14) a pyrazolyloxy group having, on the ring, 1 to 3 substituting groups which may be the same or different and are selected from the group consisting of (a) a halogen atom, (b) a cyano group, (c) a nitro group, (d) a $(C_1\text{-}C_6)$ alkyl group, (e) a halo $(C_1\text{-}C_6)$ alkyl group, (f) a $(C_1\text{-}C_6)$ alkoxy group, (g) a halo $(C_1\text{-}C_6)$ alkoxy group and (h) a formyl group;
(f15) a quinolyloxy group;
(f16) a quinolyloxy group having, on the ring, 1 to 6 substituting groups which may be the same or different and are selected from the group consisting of (a) a halogen atom, (b) a cyano group, (c) a nitro group, (d) a $(C_1\text{-}C_6)$ alkyl group, (e) a halo $(C_1\text{-}C_6)$ alkyl group, (f) a $(C_1\text{-}C_6)$ alkoxy group and (g) a halo $(C_1\text{-}C_6)$ alkoxy group;
(f17) a quinoxalyloxy group;
(f18) a quinoxalyloxy group having, on the ring, 1 to 5 substituting groups which may be the same or different and are selected from the group consisting of (a) a halogen atom, (b) a cyano group, (c) a nitro group, (d) a $(C_1\text{-}C_6)$ alkyl group, (e) a halo $(C_1\text{-}C_6)$ alkyl group, (f) a $(C_1\text{-}C_6)$ alkoxy group and (g) a halo $(C_1\text{-}C_6)$ alkoxy group;
(f19) a benzoxazolyloxy group;
(f20) a benzoxazolyloxy group having, on the ring, 1 to 4 substituting groups which may be the same or different and are selected from the group consisting of (a) a halogen atom, (b) a cyano group, (c) a nitro group, (d) a $(C_1\text{-}C_6)$ alkyl group, (e) a halo $(C_1\text{-}C_6)$ alkyl group, (f) a $(C_1\text{-}C_6)$ alkoxy group and (g) a halo $(C_1\text{-}C_6)$ alkoxy group;
(f21) a benzothiazolyloxy group; or
(f22) a benzothiazolyloxy group having, on the ring, 1 to 4 substituting groups which may be the same or different and are selected from the group consisting of (a) a halogen atom, (b) a cyano group, (c) a nitro group, (d) a $(C_1\text{-}C_6)$ alkyl group, (e) a halo $(C_1\text{-}C_6)$ alkyl group, (f) a $(C_1\text{-}C_6)$ alkoxy group and (g) a halo $(C_1\text{-}C_6)$ alkoxy group}, or a salt thereof.

[2] The endoparasite control agent according to the above [1], wherein
A represents a nitrogen atom or a C—H group,
$X^1$ and $X^2$ may be the same or different, and each represent
(a1) a hydrogen atom;
(a2) a halogen atom; or
(a4) a halo $(C_1\text{-}C_6)$ alkyl group,
$R^1$ and $R^2$ each represent (b1) a hydrogen atom,
$R^3$ and $R^4$ may be the same or different, and are selected from the group consisting of
(c1) a hydrogen atom;
(c3) a $(C_1\text{-}C_6)$ alkyl group; and
(c4) a $(C_1\text{-}C_6)$ alkoxy group, or optionally
(c6) $R^3$ and $R^4$ together with the carbon atom bound to $R^3$ and $R^4$ form a $(C_3\text{-}C_6)$ cycloalkane,
$Y^1$ represents (d2) a halogen atom,
$Y^2$ and $Y^4$ each represent (e1) a hydrogen atom, and
$Y^3$ is selected from the group consisting of
(f1) a phenyl group;
(f2) a phenyl group having, on the ring, 1 to 5 substituting groups which may be the same or different and are selected from the group consisting of (a) a halogen atom, (b) a cyano group, (c) a nitro group, (d) a $(C_1\text{-}C_6)$ alkyl group, (e) a halo ($C_1$-$C_6$) alkyl group, (f) a ($C_1$-$C_6$) alkoxy group and (g) a halo ($C_1$-$C_6$) alkoxy group;
(f3) a phenoxy group;
(f4) a phenoxy group having, on the ring, 1 to 5 substituting groups which may be the same or different and are selected from the group consisting of (a) a halogen atom, (b) a cyano group, (c) a nitro group, (d) a ($C_1$-$C_6$) alkyl group, (f) a ($C_1$-$C_6$) alkoxy group and (g) a halo ($C_1$-$C_6$) alkoxy group;
(f5) a pyridyl group;
(f7) a pyridyloxy group;
(f8) a pyridyloxy group having, on the ring, 1 to 4 substituting groups which may be the same or different and are selected from the group consisting of (a) a halogen atom, (b) a cyano group, (c) a nitro group, (d) a ($C_1$-$C_6$) alkyl group, (e) a halo ($C_1$-$C_6$) alkyl group, (f) a ($C_1$-$C_6$) alkoxy group and (g) a halo ($C_1$-$C_6$) alkoxy group;
(f10) a pyrimidyloxy group having, on the ring, 1 to 3 substituting groups which may be the same or different and are selected from the group consisting of (a) a halogen atom, (b) a cyano group, (c) a nitro group, (d) a ($C_1$-$C_6$) alkyl group, (e) a halo ($C_1$-$C_6$) alkyl group, (f) a ($C_1$-$C_6$) alkoxy group and (g) a halo ($C_1$-$C_6$) alkoxy group;
(f11) a pyrazyloxy group;
(f12) a pyrazyloxy group having, on the ring, 1 to 3 substituting groups which may be the same or different and are selected from the group consisting of (a) a halogen atom, (b) a cyano group, (c) a nitro group, (d) a ($C_1$-$C_6$) alkyl group, (e) a halo ($C_1$-$C_6$) alkyl group, (f) a ($C_1$-$C_6$) alkoxy group and (g) a halo ($C_1$-$C_6$) alkoxy group;
(f14) a pyrazolyloxy group having, on the ring, 1 to 3 substituting groups which may be the same or different and are selected from the group consisting of (a) a halogen atom, (b) a cyano group, (c) a nitro group, (d) a ($C_1$-$C_6$) alkyl group, (e) a halo ($C_1$-$C_6$) alkyl group, (f) a ($C_1$-$C_6$) alkoxy group, (g) a halo ($C_1$-$C_6$) alkoxy group and (h) a formyl group;
(f15) a quinolyloxy group;
(f17) a quinoxalyloxy group;
(f19) a benzoxazolyloxy group;
(f21) a benzothizaolyloxy group; and
(f22) a benzothizolyloxy group having, on the ring, 1 to 4 substituting groups which may be the same or different and are selected from the group consisting of (a) a halogen atom, (b) a cyano group, (c) a nitro group, (d) a ($C_1$-$C_6$) alkyl group, (e) a halo ($C_1$-$C_6$) alkyl group, (f) a ($C_1$-$C_6$) alkoxy group and (g) a halo ($C_1$-$C_6$) alkoxy group.
(3) The endoparasite control agent according to the above [1], wherein
A represents a C—H group,
$X^1$ and $X^2$ may be the same or different, and are selected from the group consisting of
(a1) a hydrogen atom;
(a2) a halogen atom; and
(a4) a halo ($C_1$-$C_6$) alkyl group,
$R^1$ and $R^2$ each represent (b1) a hydrogen atom,
$R^3$ and $R^4$ may be the same or different, and are selected from the group consisting of
(c1) a hydrogen atom;
(c3) a ($C_1$-$C_6$) alkyl group; and
(c4) a ($C_1$-$C_6$) alkoxy group, or optionally
(c6) $R^3$ and $R^4$ together with the carbon atom bound to $R^3$ and $R^4$ form a ($C_3$-$C_6$) cycloalkane,
$Y^1$ represents (d2) a halogen atom,
$Y^2$ and $Y^4$ each represent (e1) a hydrogen atom, and
$Y^3$ is selected from the group consisting of (f1) a phenyl group;
(f2) a phenyl group having, on the ring, 1 to 5 substituting groups which may be the same or different and are selected from the group consisting of (a) a halogen atom, (b) a cyano group, (c) a nitro group, (d) a ($C_1$-$C_6$) alkyl group, (e) a halo ($C_1$-$C_6$) alkyl group, (f) a ($C_1$-$C_6$) alkoxy group and (g) a halo ($C_1$-$C_6$) alkoxy group;
(f3) a phenoxy group;
(f4) a phenoxy group having, on the ring, 1 to 5 substituting groups which may be the same or different and are selected from the group consisting of (a) a halogen atom, (b) a cyano group, (c) a nitro group, (d) a ($C_1$-$C_6$) alkyl group, (f) a ($C_1$-$C_6$) alkoxy group and (g) a halo ($C_1$-$C_6$) alkoxy group;
(f5) a pyridyl group;
(f7) a pyridyloxy group;
(f8) a pyridyloxy group having, on the ring, 1 to 4 substituting groups which may be the same or different and are selected from the group consisting of (a) a halogen atom, (b) a cyano group, (c) a nitro group, (d) a ($C_1$-$C_6$) alkyl group, (e) a halo ($C_1$-$C_6$) alkyl group, (f) a ($C_1$-$C_6$) alkoxy group and (g) a halo ($C_1$-$C_6$) alkoxy group;
(f10) a pyrimidyloxy group having, on the ring, 1 to 3 substituting groups which may be the same or different and are selected from the group consisting of (a) a halogen atom, (b) a cyano group, (c) a nitro group, (d) a ($C_1$-$C_6$) alkyl group, (e) a halo ($C_1$-$C_6$) alkyl group, (f) a ($C_1$-$C_6$) alkoxy group and (g) a halo ($C_1$-$C_6$) alkoxy group;
(f11) a pyrazyloxy group;
(f12) a pyrazyloxy group having, on the ring, 1 to 3 substituting groups which may be the same or different and are selected from the group consisting of (a) a halogen atom, (b) a cyano group, (c) a nitro group, (d) a ($C_1$-$C_6$) alkyl group, (e) a halo ($C_1$-$C_6$) alkyl group, (f) a ($C_1$-$C_6$) alkoxy group and (g) a halo ($C_1$-$C_6$) alkoxy group;
(f14) a pyrazolyloxy group having, on the ring, 1 to 3 substituting groups which may be the same or different and are selected from the group consisting of (a) a halogen atom, (b) a cyano group, (c) a nitro group, (d) a ($C_1$-$C_6$) alkyl group, (e) a halo ($C_1$-$C_6$) alkyl group, (f) a ($C_1$-$C_6$) alkoxy group, (g) a halo ($C_1$-$C_6$) alkoxy group and (h) a formyl group;
(f15) a quinolyloxy group;
(f17) a quinoxalyloxy group;
(f18) a benzoxazolyloxy group;
(f21) a benzothiazolyloxy group; and
(f22) a benzothiazolyloxy group having, on the ring, 1 to 4 substituting groups which may be the same or different and are selected from the group consisting of (a) a halogen atom, (b) a cyano group, (c) a nitro group, (d) a ($C_1$-$C_6$) alkyl group, (e) a halo ($C_1$-$C_6$) alkyl group, (f) a ($C_1$-$C_6$) alkoxy group and (g) a halo ($C_1$-$C_6$) alkoxy group.
[4] The endoparasite control agent according to the above [1], wherein
A represents a nitrogen atom,
$X^1$ and $X^2$ may be the same or different, and are selected from the group consisting of
(a1) a hydrogen atom;
(a2) a halogen atom; and
(a4) a halo ($C_1$-$C_6$) alkyl group,
$R^1$ and $R^2$ each represent (b1) a hydrogen atom,
$R^3$ and $R^4$ may be the same or different, and are selected from the group consisting of
(c1) a hydrogen atom; and
(c3) a ($C_1$-$C_6$) alkyl group,
$Y^1$ represents
(d2) a halogen atom; or
(d3) a ($C_1$-$C_6$) alkyl group, Y² and Y⁴ each represent (e1) a hydrogen atom, and
Y³ is selected from the group consisting of
(f1) a phenyl group;
(f2) a phenyl group having, on the ring, 1 to 5 substituting groups which may be the same or different and are selected from the group consisting of (a) a halogen atom, (b) a cyano group, (c) a nitro group, (d) a ($C_1$-$C_6$) alkyl group, (e) a halo ($C_1$-$C_6$) alkyl group, (f) a ($C_1$-$C_6$) alkoxy group and (g) a halo ($C_1$-$C_6$) alkoxy group;
(f3) a phenoxy group;
(f4) a phenoxy group having, on the ring, 1 to 5 substituting groups which may be the same or different and are selected from the group consisting of (a) a halogen atom, (b) a cyano group, (c) a nitro group, (d) a ($C_1$-$C_6$) alkyl group, (f) a ($C_1$-$C_6$) alkoxy group and (g) a halo ($C_1$-$C_6$) alkoxy group; and
(f5) a pyridyl group.
[5] A method for controlling endoparasites, comprising orally or parenterally administering an effective amount of the endoparasite control agent according to any one of the above [1] to [4] to a non-human mammal or a bird.
[6] A method for controlling endoparasites, comprising orally or parenterally administering an effective amount of the endoparasite control agent according to any one of the above [1] to [4] to a non-human mammal.
[7] The method according to the above [5] or [6], wherein the non-human mammal is a domestic animal.
[8] A method for controlling endoparasites, comprising orally or parenterally administering an effective amount of the endoparasite control agent according to any one of the above [1] to [4] to a human.
[9] The carboxamide derivative specified in any one of the above [1] to [4] or a salt thereof for use in control of endoparasites.
[10] Use of the carboxamide derivative specified in any one of the above [1] to [4] or a salt thereof for production of endoparasite control agents.
[11] Use of the carboxamide derivative specified in any one of the above [1] to [4] or a salt thereof for control of endoparasites.

Advantageous Effects of Invention

The present invention provides an endoparasite control agent having better performance in the disinfection or control of endoparasites as compared with the conventional art.

DESCRIPTION OF EMBODIMENTS

The definitions in connection with the general formula (I) representing the carboxamide derivative of the present invention are described below.

The "halogen atom" refers to a chlorine atom, a bromine atom, an iodine atom or a fluorine atom.

The "($C_1$-$C_6$) alkyl group" refers to a straight-chain or branched-chain alkyl group of 1 to 6 carbon atoms, for example, a methyl group, an ethyl group, a n-propyl group, an isopropyl group, a n-butyl group, an isobutyl group, a sec-butyl group, a tert-butyl group, a n-pentyl group, a neopentyl group, a n-hexyl group or the like.

The "($C_1$-$C_6$) alkoxy group" refers to a straight-chain or branched-chain alkoxy group of 1 to 6 carbon atoms, for example, a methoxy group, an ethoxy group, a n-propoxy group, an isopropoxy group, a n-butoxy group, a sec-butoxy group, a tert-butoxy group, a n-pentyloxy group, an isopentyloxy group, a neopentyloxy group, a n-hexyloxy group or the like.

The "halo ($C_1$-$C_6$) alkyl group" refers to a straight-chain or branched-chain alkyl group of 1 to 6 carbon atoms substituted with one or more halogen atoms which may be the same or different from each other, for example, a trifluoromethyl group, a difluoromethyl group, a perfluoroethyl group, a hexafluoroisopropyl group, a perfluoroisopropyl group, a chloromethyl group, a bromomethyl group, a 1-bromoethyl group, a 2,3-dibromopropyl group or the like.

The "halo ($C_1$-$C_6$) alkoxy group" refers to a straight-chain or branched-chain alkoxy group of 1 to 6 carbon atoms substituted with one or more halogen atoms which may be the same or different from each other, for example, a trifluoromethoxy group, a difluoromethoxy group, a perfluoroethoxy group, a perfluoroisopropoxy group, a chloromethoxy group, a bromomethoxy group, a 1-bromoethoxy group, a 2,3-dibromopropoxy group or the like.

The "($C_3$-$C_6$) cycloalkane" formed of $R^1$ and $R_2$ together with the carbon atom bound to $R^1$ and $R^2$ is, for example, cyclopropane, cyclobutane, cyclopentane, cyclohexane or the like.

The "($C_3$-$C_6$) cycloalkane" formed of $R^3$ and $R^4$ together with the carbon atom bound to $R^3$ and $R_4$ is, for example, cyclopropane, cyclobutane, cyclopentane, cyclohexane or the like.

Examples of the salt of the carboxamide derivative represented by the general formula (I) of the present invention include inorganic acid salts, such as hydrochlorides, sulfates, nitrates and phosphates; organic acid salts, such as acetates, fumarates, maleates, oxalates, methanesulfonates, benzenesulfonates and p-toluenesulfonates; and salts with an inorganic or organic base such as a sodium ion, a potassium ion, a calcium ion and a trimethylammonium ion.

As the carboxamide derivative of the present invention, preferred is a compound of the general formula (I) in which
A represents a nitrogen atom or a C—H group,
$X^1$ and $X^2$ may be the same or different, and each represent
(a1) a hydrogen atom;
(a2) a halogen atom; or
(a4) a halo ($C_1$-$C_6$) alkyl group,
$R^1$ and $R^2$ each represent (b1) a hydrogen atom,
$R^3$ and $R^4$ may be the same or different, and are selected from the group consisting of
(c1) a hydrogen atom;
(c3) a ($C_1$-$C_6$) alkyl group; and
(c4) a ($C_1$-$C_6$) alkoxy group, or optionally
(c6) $R^3$ and $R^4$ together with the carbon atom bound to $R^3$ and $R^4$ form a ($C_3$-$C_6$) cycloalkane,
$Y^1$ represents (d2) a halogen atom,
$Y^2$ and $Y^4$ each represent (e1) a hydrogen atom, and
$Y^3$ is selected from the group consisting of
(f1) a phenyl group;
(f2) a phenyl group having, on the ring, 1 to 5 substituting groups which may be the same or different and are selected from the group consisting of (a) a halogen atom, (b) a cyano group, (c) a nitro group, (d) a ($C_1$-$C_6$) alkyl group, (e) a halo ($C_1$-$C_6$) alkyl group, (f) a ($C_1$-$C_6$) alkoxy group and (g) a halo ($C_1$-$C_6$) alkoxy group;
(f3) a phenoxy group;
(f4) a phenoxy group having, on the ring, 1 to 5 substituting groups which may be the same or different and are selected from the group consisting of (a) a halogen atom, (b) a cyano group, (c) a nitro group, (d) a ($C_1$-$C_6$) alkyl group, (f) a ($C_1$-$C_6$) alkoxy group and (g) a halo ($C_1$-$C_6$) alkoxy group;
(f5) a pyridyl group;

(f7) a pyridyloxy group;
(f8) a pyridyloxy group having, on the ring, 1 to 4 substituting groups which may be the same or different and are selected from the group consisting of (a) a halogen atom, (b) a cyano group, (c) a nitro group, (d) a ($C_1$-$C_6$) alkyl group, (e) a halo ($C_1$-$C_6$) alkyl group. If) a ($C_1$-$C_6$) alkoxy group and (g) a halo ($C_1$-$C_6$) alkoxy group;
(f10) a pyrimidyloxy group having, on the ring, 1 to 3 substituting groups which may be the same or different and are selected from the group consisting of (a) a halogen atom, (b) a cyano group, (c) a nitro group, (d) a ($C_1$-$C_6$) alkyl group, (e) a halo ($C_1$-$C_6$) alkyl group, (f) a ($C_1$-$C_6$) alkoxy group and (g) a halo ($C_1$-$C_6$) alkoxy group;
(f11) a pyrazyloxy group;
(f12) a pyrazyloxy group having, on the ring, 1 to 3 substituting groups which may be the same or different and are selected from the group consisting of (a) a halogen atom, (b) a cyano group, (c) a nitro group, (d) a ($C_1$-$C_6$) alkyl group, (e) a halo ($C_1$-$C_6$) alkyl group, (f) a ($C_1$-$C_6$) alkoxy group and (g) a halo ($C_1$-$C_6$) alkoxy group;
(f14) a pyrazolyloxy group having, on the ring, 1 to 3 substituting groups which may be the same or different and are selected from the group consisting of (a) a halogen atom, (b) a cyano group, (c) a nitro group, (d) a ($C_1$-$C_6$) alkyl group, (e) a halo ($C_1$-$C_6$) alkyl group, (f) a ($C_1$-$C_6$) alkoxy group, (g) a halo ($C_1$-$C_6$) alkoxy group and (h) a formyl group;
(f15) a quinolyloxy group;
(f17) a quinoxalyloxy group;
(f19) a benzoxazolyloxy group;
(f21) a benzothiazolyloxy group; and
(f22) a benzothiazolyloxy group having, on the ring, 1 to 4 substituting groups which may be the same or different and are selected from the group consisting of (a) a halogen atom, (b) a cyano group, (c) a nitro group, (d) a ($C_1$-$C_6$) alkyl group, (e) a halo ($C_1$-$C_6$) alkyl group, (f) a ($C_1$-$C_6$) alkoxy group and (g) a halo ($C_1$-$C_6$) alkoxy group, or a salt thereof.

As the carboxamide derivative of the present invention, further preferred is a compound of the general formula (I) in which A represents a C—H group, $X^1$ and $X^2$ may be the same or different, and are selected from the group consisting of (a1) a hydrogen atom;
(a2) a halogen atom; and
(a4) a halo ($C_1$-$C_6$) alkyl group, $R^1$ and $R^2$ each represent (b1) a hydrogen atom, $R^3$ and $R^4$ may be the same or different, and are selected from the group consisting of (c1) a hydrogen atom;
(c3) a ($C_1$-$C_6$) alkyl group; and
(c4) a ($C_1$-$C_6$) alkoxy group, or optionally
(c6) $R^3$ and $R^4$ together with the carbon atom bound to $R^3$ and $R^4$ form a ($C_3$-$C_6$) cycloalkane, $Y^1$ represents (d2) a halogen atom, $Y^2$ and $Y^4$ each represent (e1) a hydrogen atom, and $Y^3$ is selected from the group consisting of (f1) a phenyl group;
(f2) a phenyl group having, on the ring, 1 to 5 substituting groups which may be the same or different and are selected from the group consisting of (a) a halogen atom, (b) a cyano group, (c) a nitro group, (d) a ($C_1$-$C_6$) alkyl group, (e) a halo ($C_1$-$C_6$) alkyl group, (f) a ($C_1$-$C_6$) alkoxy group and (g) a halo ($C_1$-$C_6$) alkoxy group;
(f3) a phenoxy group;
(f4) a phenoxy group having, on the ring, 1 to 5 substituting groups which may be the same or different and are selected from the group consisting of (a) a halogen atom, (b) a cyano group, (c) a nitro group, (d) a ($C_1$-$C_6$) alkyl group, (f) a ($C_1$-$C_6$) alkoxy group and (g) a halo ($C_1$-$C_6$) alkoxy group;
(f5) a pyridyl group;
(f7) a pyridyloxy group;
(f8) a pyridyloxy group having, on the ring, 1 to 4 substituting groups which may be the same or different and are selected from the group consisting of (a) a halogen atom, (b) a cyano group, (c) a nitro group, (d) a ($C_1$-$C_6$) alkyl group, (e) a halo ($C_1$-$C_6$) alkyl group, (f) a ($C_1$-$C_6$) alkoxy group and (g) a halo ($C_1$-$C_6$) alkoxy group;
(f10) a pyrimidyloxy group having, on the ring, 1 to 3 substituting groups which may be the same or different and are selected from the group consisting of (a) a halogen atom, (b) a cyano group, (c) a nitro group, (d) a ($C_1$-$C_6$) alkyl group, (e) a halo ($C_1$-$C_6$) alkyl group, (f) a ($C_1$-$C_6$) alkoxy group and (g) a halo ($C_1$-$C_6$) alkoxy group;
(f11) a pyrazyloxy group;
(f12) a pyrazyloxy group having, on the ring, 1 to 3 substituting groups which may be the same or different and are selected from the group consisting of (a) a halogen atom, (b) a cyano group, (c) a nitro group, (d) a ($C_1$-$C_6$) alkyl group, (e) a halo ($C_1$-$C_6$) alkyl group, (f) a ($C_1$-$C_6$) alkoxy group and (g) a halo ($C_1$-$C_6$) alkoxy group;
(e14) a pyrazolyloxy group having, on the ring, 1 to 3 substituting groups which may be the same or different and are selected from the group consisting of (a) a halogen atom, (b) a cyano group, (c) a nitro group, (d) a ($C_1$-$C_6$) alkyl group, (e) a halo ($C_1$-$C_6$) alkyl group, (f) a ($C_1$-$C_6$) alkoxy group, (g) a halo ($C_1$-$C_6$) alkoxy group and (h) a formyl group;
(f15) a quinolyloxy group;
(f17) a quinoxalyloxy group;
(f19) a benzoxazolyloxy group;
(f21) a benzothiazolyloxy group; and
(f22) a benzothiazolyloxy group having, on the ring, 1 to 4 substituting groups which may be the same or different and are selected from the group consisting of (a) a halogen atom, (b) a cyano group, (c) a nitro group, (d) a ($C_1$-$C_6$) alkyl group, (e) a halo ($C_1$-$C_6$) alkyl group, (f) a ($C_1$-$C_6$) alkoxy group and (g) a halo ($C_1$-$C_6$) alkoxy group, or a salt thereof.

Also preferred is a compound of the general formula (I) in which

A represents a nitrogen atom, $X^1$ and $X^2$ may be the same or different, and are selected from the group consisting of (a1) a hydrogen atom;
(a2) a halogen atom; and
(a4) a halo ($C_1$-$C_6$) alkyl group, $R^1$ and $R^2$ each represent (b1) a hydrogen atom, $R^3$ and $R^4$ may be the same or different, and are selected from the group consisting of (c1) a hydrogen atom; and
(c3) a ($C_1$-$C_6$) alkyl group, $Y^1$ represents (d2) a halogen atom; or
(d3) a ($C_1$-$C_6$) alkyl group, $Y^2$ and $Y^4$ each represent (e1) a hydrogen atom, and $Y^3$ is selected from the group consisting of (f1) a phenyl group;
(f2) a phenyl group having, on the ring, 1 to 5 substituting groups which may be the same or different and are selected from the group consisting of (a) a halogen atom, (b) a cyano group, (c) a nitro group, (d) a ($C_1$-$C_6$) alkyl group, (e) a halo ($C_1$-$C_6$) alkyl group, (f) a ($C_1$-$C_6$) alkoxy group and (g) a halo ($C_1$-$C_6$) alkoxy group;

(f3) a phenoxy group;

(f4) a phenoxy group having, on the ring, 1 to 5 substituting groups which may be the same or different and are selected from the group consisting of (a) a halogen atom, (b) a cyano group, (c) a nitro group, (d) a ($C_1$-$C_6$) alkyl group, (f) a ($C_1$-$C_6$) alkoxy group and (g) a halo ($C_1$-$C_6$) alkoxy group; and (f5) a pyridyl group, or a salt thereof.

The compound represented by the general formula (I) of the present invention can be produced by any of the production methods described in JP-A 01-151546, WO 2007/060162, JP-A 53-9739, WO 2007/108483, WO 2008/101975, WO 2008/101976, WO 2009/003745, WO 2008/003746, WO 2009/012998, WO 2009/127718, WO 2010/106971 and WO 2012/118139, the method described in Shin-Jikken Kagaku Kouza 14 (Maruzen, Dec. 20, 1977), a modified method of the foregoing, or the like.

Representative examples of the carboxamide derivative represented by the general formula (I) of the present invention are shown in Tables 1 and 2, but the present invention is not limited thereto. In Tables 1 and 2, "MeO" stands for a methoxy group, "Ph" stands for a phenyl group, "Py" stands for a pyridyl group, "PhO" stands for a phenoxy group, and "PyO" stands for a pyridyloxy group. Shown in the column of "Physical property" are mass spectral data.

Q1 to Q19 represent the following structures. The black circle in each of the formulae Q1 to Q19 represents a binding site.

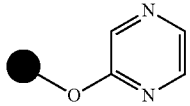 Q1

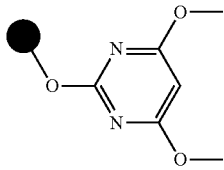 Q2

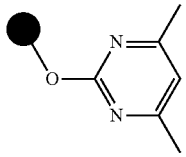 Q3

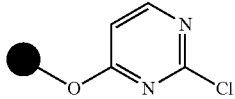 Q4

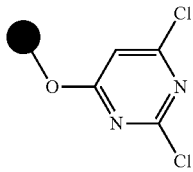 Q5

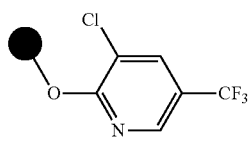 Q6

-continued

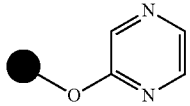 Q7

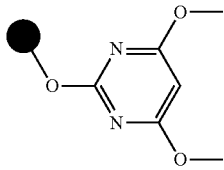 Q8

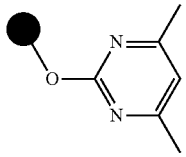 Q9

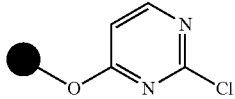 Q10

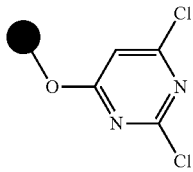 Q11

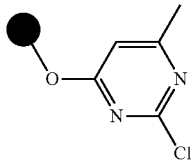 Q12

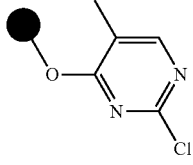 Q13

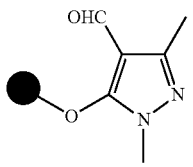 Q14

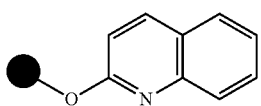 Q15

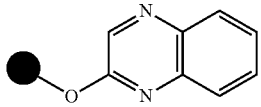 Q16

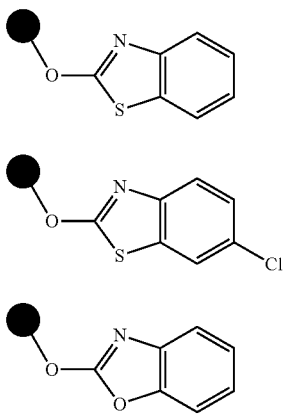

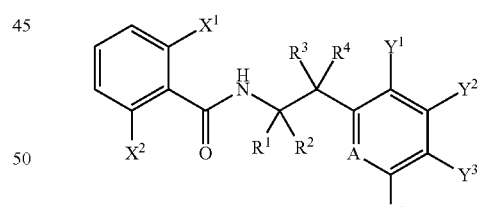

TABLE 1

| Compound No. | X¹ | X² | R³ | R⁴ | Y¹ | Y³ | Physical property |
|---|---|---|---|---|---|---|---|
| 1-1 | CF$_3$ | H | H | H | Cl | Q3 | 489 (M + 1) |
| 1-2 | CF$_3$ | H | H | H | Cl | Q4 | 535 (M + 1) |
| 1-3 | CF$_3$ | H | H | H | Cl | Q5 | 490 (M + 1) |
| 1-4 | CF$_3$ | H | H | H | Cl | Q6 | 456 (M + 1) |
| 1-5 | CF$_3$ | H | H | H | Cl | Q7 | 422 (M + 1) |
| 1-6 | CF$_3$ | H | H | H | Cl | Q8 | 482 (M + 1) |
| 1-7 | CF$_3$ | H | H | H | Cl | Q9 | 450 (M + 1) |
| 1-8 | CF$_3$ | H | H | H | Cl | Q10 | 456 (M + 1) |
| 1-9 | CF$_3$ | H | H | H | Cl | Q11 | 490 (M + 1) |
| 1-10 | CF$_3$ | H | H | H | Cl | Q12 | 470 (M + 1) |
| 1-11 | CF$_3$ | H | H | H | Cl | Q13 | 470 (M + 1) |
| 1-12 | CF$_3$ | H | H | H | Cl | Q14 | 466 (M + 1) |
| 1-13 | CF$_3$ | H | H | H | Cl | Q15 | 471 (M + 1) |
| 1-14 | CF$_3$ | H | H | H | Cl | Q16 | 472 (M + 1) |
| 1-15 | CF$_3$ | H | H | H | Cl | Q17 | 477 (M + 1) |
| 1-16 | CF$_3$ | H | H | H | Cl | Q18 | 511 (M + 1) |
| 1-17 | CF$_3$ | H | H | H | Cl | Q19 | 461 (M + 1) |
| 1-18 | CF$_3$ | H | H | H | Cl | PhO | 420 (M + 1) |
| 1-19 | CF$_3$ | H | H | H | Cl | 4-CF$_3$—PhO | 488 (M + 1) |
| 1-20 | I | H | H | H | Cl | Q1 | 581 (M + 1) |
| 1-21 | I | H | H | H | Cl | Q2 | 547 (M + 1) |
| 1-22 | I | H | H | H | Cl | Q3 | 547 (M + 1) |
| 1-23 | I | H | H | H | Cl | Q4 | 593 (M + 1) |
| 1-24 | I | H | H | H | Cl | Q5 | 548 (M + 1) |
| 1-25 | I | H | H | H | Cl | Q6 | 514 (M + 1) |
| 1-26 | I | H | H | H | Cl | Q7 | 480 (M + 1) |
| 1-27 | I | H | H | H | Cl | Q8 | 540 (M + 1) |
| 1-28 | I | H | H | H | Cl | Q9 | 508 (M + 1) |
| 1-29 | I | H | H | H | Cl | Q10 | 514 (M + 1) |
| 1-30 | I | H | H | H | Cl | Q11 | 550 (M + 1) |
| 1-31 | I | H | H | H | Cl | Q12 | 528 (M + 1) |
| 1-32 | I | H | H | H | Cl | Q13 | 528 (M + 1) |
| 1-33 | I | H | H | H | Cl | Q14 | 524 (M + 1) |
| 1-34 | I | H | H | H | Cl | Q15 | 529 (M + 1) |
| 1-35 | I | H | H | H | Cl | Q16 | 530 (M + 1) |
| 1-36 | I | H | H | H | Cl | Q17 | 535 (M + 1) |
| 1-37 | I | H | H | H | Cl | Q18 | 569 (M + 1) |
| 1-38 | I | H | H | H | Cl | Q19 | 519 (M + 1) |
| 1-39 | I | H | H | H | Cl | PhO | 478 (M + 1) |
| 1-40 | I | H | H | H | Cl | 4-CF$_3$—PhO | 546 (M + 1) |
| 1-41 | CF$_3$ | H | Me | H | Cl | Q1 | 537 (M + 1) |
| 1-42 | CF$_3$ | H | Me | H | Cl | Q2 | 503 (M + 1) |
| 1-43 | CF$_3$ | H | Me | H | Cl | Q3 | 503 (M + 1) |
| 1-44 | CF$_3$ | H | Me | Me | Cl | Q1 | 551 (M + 1) |
| 1-45 | CF$_3$ | H | Me | Me | Cl | Q2 | 517 (M + 1) |
| 1-46 | CF$_3$ | H | Me | Me | Cl | Q3 | 517 (M + 1) |
| 1-47 | CF$_3$ | H | CH$_2$CH$_2$ | | Cl | Q1 | 549 (M + 1) |
| 1-48 | CF$_3$ | H | CH$_2$CH$_2$ | | Cl | Q2 | 515 (M + 1) |
| 1-49 | CF$_3$ | H | CH$_2$CH$_2$ | | Cl | Q3 | 515 (M + 1) |
| 1-50 | CF$_3$ | H | H | H | Cl | 4-CF$_3$—Ph | 472 (M + 1) |
| 1-51 | CF$_3$ | H | H | H | Cl | 3-CF$_3$—Ph | 472 (M + 1) |
| 1-52 | CF$_3$ | H | H | H | Cl | 3,5-F$_2$—Ph | 440 (M + 1) |
| 1-53 | CF$_3$ | H | H | H | Cl | 4-MeO—Ph | 434 (M + 1) |
| 1-54 | CF$_3$ | H | H | H | Cl | Ph | 404 (M + 1) |
| 1-55 | CF$_3$ | H | H | H | Cl | 4-Py | 405 (M + 1) |
| 1-56 | CF$_3$ | H | H | H | Cl | 3-Py | 405 (M + 1) |
| 1-57 | CF$_3$ | H | Me | H | Cl | 4-CF$_3$—Ph | 486 (M + 1) |
| 1-58 | CF$_3$ | H | Me | H | Cl | Ph | 418 (M + 1) |
| 1-59 | CF$_3$ | H | Me | H | Cl | 4-Py | 419 (M + 1) |
| 1-60 | CF$_3$ | H | MeO | H | Cl | Q1 | 553 (M + 1) |
| 1-61 | CF$_3$ | H | MeO | H | Cl | Q2 | 519 (M + 1) |
| 1-62 | CF$_3$ | H | MeO | H | Cl | Q3 | 521 (M + 1) |
| 1-63 | CF$_3$ | H | MeO | H | Cl | Q17 | 507 (M + 1) |
| 1-64 | CF$_3$ | H | MeO | H | Cl | PhO | 418 (—MeOH) |
| 1-65 | CF$_3$ | H | MeO | H | Cl | 4-CF$_3$—PhO | 518 (M + 1) |
| 1-66 | CF$_3$ | H | MeO | H | Cl | 4-MeO—Ph | 448 (—MeOH) |
| 1-67 | CF$_3$ | H | MeO | H | Cl | 3-PyO | 451 (M + 1) |
| 1-68 | F | F | Me | H | Cl | Q1 | 505 (M + 1) |
| 1-69 | F | F | Me | H | Cl | Q2 | 471 (M + 1) |
| 1-70 | F | F | Me | H | Cl | Q3 | 471 (M + 1) |
| 1-71 | F | F | Me | Me | Cl | Q1 | 519 (M + 1) |
| 1-72 | F | F | Me | Me | Cl | Q2 | 485 (M + 1) |
| 1-73 | F | F | Me | Me | Cl | Q3 | 485 (M + 1) |
| 1-74 | F | F | CH$_2$CH$_2$ | | Cl | Q3 | 517 (M + 1) |
| 1-75 | F | F | CH$_2$CH$_2$ | | Cl | Q2 | 483 (M + 1) |
| 1-76 | F | F | CH$_2$CH$_2$ | | Cl | Q3 | 483 (M + 1) |
| 1-77 | CF$_3$ | H | Me | Me | Me | Q1 | 531 (M + 1) |
| 1-78 | CF$_3$ | H | Me | Me | Me | Q2 | 497 (M + 1) |
| 1-79 | I | H | Me | Me | Me | Q1 | 589 (M + 1) |
| 1-80 | F | F | Me | Me | Me | Q1 | 499 (M + 1) |

In Table 1, R¹, R², Y² and Y⁴ represent H, and A represents CH.

TABLE 2

| Compound No. | X¹ | R³ | R⁴ | Y¹ | Y³ | Physical property |
|---|---|---|---|---|---|---|
| 2-1 | CF$_3$ | H | H | Cl | Ph | 405 (M + 1) |
| 2-2 | CF$_3$ | H | H | Cl | 4-CF$_3$—Ph | 473 (M + 1) |
| 2-3 | CF$_3$ | H | H | Cl | 3-CF$_3$—Ph | 473 (M + 1) |
| 2-4 | CF$_3$ | H | H | Cl | 3,5-F$_2$—Ph | 441 (M + 1) |
| 2-5 | CF$_3$ | H | H | Cl | 4-MeO—Ph | 435 (M + 1) |
| 2-6 | CF$_3$ | H | H | Cl | 4-Py | 406 (M + 1) |
| 2-7 | CF$_3$ | H | H | Cl | 3-Py | 406 (M + 1) |
| 2-8 | CF$_3$ | Me | H | Cl | Ph | 419 (M + 1) |
| 2-9 | CF$_3$ | Me | H | Cl | 4-CF$_3$—Ph | 487 (M + 1) |

TABLE 2-continued

| Compound No. | $X^1$ | $R^3$ | $R^4$ | $Y^1$ | $Y^3$ | Physical property |
|---|---|---|---|---|---|---|
| 2-10 | $CF_3$ | Me | H | Cl | 3-$CF_3$—Ph | 487 (M + 1) |
| 2-11 | $CF_3$ | Me | H | Cl | 3,5-$F_2$—Ph | 455 (M + 1) |
| 2-12 | $CF_3$ | Me | Me | Cl | Ph | 433 (M + 1) |
| 2-13 | $CF_3$ | Me | Me | Cl | 4-$CF_3$—Ph | 501 (M + 1) |
| 2-14 | $CF_3$ | Me | Me | Cl | 3-$CF_3$—Ph | 501 (M + 1) |
| 2-15 | $CF_3$ | Me | Me | Cl | 3,5-$F_2$—Ph | 469 (M + 1) |
| 2-16 | I | H | H | Cl | Ph | 463 (M + 1) |
| 2-17 | I | H | H | Cl | 4-$CF_3$—Ph | 531 (M + 1) |
| 2-18 | I | H | H | Cl | 3-$CF_3$—Ph | 531 (M + 1) |
| 2-19 | I | H | H | Cl | 3,5-$F_2$—Ph | 499 (M + 1) |
| 2-20 | I | H | H | Cl | 4-MeO—Ph | 493 (M + 1) |
| 2-21 | I | H | H | Cl | 4-Py | 464 (M + 1) |
| 2-22 | I | H | H | Cl | 3-Py | 464 (M + 1) |
| 2-23 | I | Me | H | Cl | Ph | 477 (M + 1) |
| 2-24 | I | Me | H | Cl | 4-$CF_3$—Ph | |
| 2-25 | I | Me | H | Cl | 3-$CF_3$—Ph | |
| 2-26 | I | Me | H | Cl | 3,5-$F_2$—Ph | |
| 2-27 | I | Me | Me | Cl | Ph | |
| 2-28 | I | Me | Me | Cl | 4-$CF_3$—Ph | |
| 2-29 | I | Me | Me | Cl | 3-$CF_3$—Ph | |
| 2-30 | I | Me | Me | Cl | 3,5-$F_2$—Ph | |

In Table 2, $X^2$, $R^1$, $R^2$, $Y^2$ and $Y^4$ represent H, and A represents a nitrogen atom.

The endoparasite control agent of the present invention has excellent anti-endoparasite effect, and exerts appropriate control effect against endoparasites. The animal for which the endoparasite control agent of the present invention can be used is a human and an animal of non-human mammalian or avian species. Exemplary members of the non-human mammalian species include domestic animals, such as pigs, horses, cattle, sheep, goats, rabbits, camels, water buffalos, deer, mink and chinchillas; pet animals, such as dogs, cats, little birds and monkeys; and experimental animals, such as rats, mice, golden hamsters and guinea pigs. Exemplary members of the avian species include domestic fowls, such as chickens, ducks, aigamo ducks (crossbreeds of wild and domestic ducks), quails, domestic ducks, geese and turkeys. The examples listed above are non-limiting examples.

Human endoparasites against which the endoparasite control agent of the present invention is effective are roughly classified into protozoa and helminths. Examples of the protozoa include, but are not limited thereto, Rhizopoda, such as *Entamoeba histolytica*; Mastigophora, such as *Leishmania*, *Trypanosoma* and *Trichomonas*; Sporozoea, such as *Plasmodium* and *Toxoplasma*; and Ciliophora, such as *Balantidium coli*. Examples of the helminths include, but are not limited thereto, Nematoda, such as *Ascaris lumbricoides*, *Anisakis*, *Toxocara canis*, *Trichostrongylus* spp., *Enterobius vermicularis*, hookworms (for example, *Ancylostoma duodenale*, *Necator americanus*, *Ancylostoma braziliense*, etc.), *Angiostrongylus* spp., *Gnathostoma* spp., filarial worms (filaria, *Wuchereria bancrofti*, *Brugia malayi*, etc.). *Onchocerca volvulus*, *Dracunculus medinensis*, *Trichinella spiralis* and *Strongyloides stercoralis*; Acanthocephala, such as *Macracanthorhynchus hirudinaceus*; Gordiacea, such as Gordioidea; Hirudinea, such as *Hirudo nipponia*; Trematoda, such as *Schistosoma japonicum*, *Schistosoma mansoni*, *Schistosoma haematobium*, *Clonorchis sinensis*, *Hateropheyes heterophyes*, *Fasciola* spp. and *Paragonimus* spp.; and Cestoda, such as *Diphyllobothrium latum*, *Sparganum mansoni*, *Sparganum proliferum*, *Diplogonoporus grandis*, Taeniidae (for example, *Taeniarhynchus saginatus*, *Taenia solium*, *Echinococcus*, etc.), *Hymenolepis* spp., *Dipylidium caninum*, *Mesocestoides lineatus*, *Bertiella* spp. and *Nybelinia surmenicola*.

Non-human mammalian or avian endoparasites against which the endoparasite control agent of the present invention is effective are roughly classified into protozoa and helminths. Examples of the protozoa include, but are not limited thereto, Apicomplexa, such as Coccidid (for example, *Eimeria*, *Isospora*, *Toxoplasma*, *Neospora*, *Sarcocystis*, *Besnoitia*, *Hammondia*, *Cryptosporidium*, *Caryospora*, etc.), Haemosporina (for example, *Leucocytozoon*, *Plasmodium*, etc.), Piroplasma (for example, *Theileria*, *Anaplasma*, *Eperythrozoon*, *Haemobartonella*, *Ehrlichia*, etc.), and others (for example, *Hepatozoon*, *Haemogregarina*, etc.); Microspora, such as *Encephalitozoon* and *Nosema*; Mastigophora, such as Trypanosomatid (for example, *Trypanosoma*, *Leishmania*, etc.), Trichotnonadida (for example, *Chilomastix*, *Trichomonas*, *Monocercomonas*, *Histomonas*, etc.), and Diplomonadida (for example, *Hexamita*, *Giardia*, etc.); Sarcodina, such as Amoebida (for example, *Entamoeba histolytica* (*Entamoeba*) etc.); and Ciliophora, such as *Balantidium coli* (*Balantidium*), *Buxtonella* and *Entodinium*.

Examples of the helminths include, but are not limited thereto, Nematoda, such as Ascaridida (for example, *Ascaris suum* (*Ascaris*), *Toxocara canis* and *Toxocara cati* (*Toxocara*), *Toxascaris leonina* (*Toxascaris*), *Parascaris equorum* (*Parascaris*), *Ascaridia galli* (*Ascaridia*), *Heterakis gallinarum* (*Heterakis*), *Anisakis*, etc.), Oxyurida (for example *Oxyuris equi* (*Oxyuris*), *Passalurus ambiguus* (*Passalurus*), etc.), Strongylida (for example, *Strongylus vulgaris* (*Strongylus*), *Haemonchus contortus* (*Haemonchus*), *Ostertagia ostertagi* (*Ostertagia*), *Trichostrongylus colubriformis* (*Trichostrongylus*), *Cooperia punctata* (*Cooperia*), *Nematodirus filicollis* (*Nematodirus*), *Hyostrongylus rubidus* (*Hyostrongylus*), *Oesophagostomum radiatum* (*Oesophagostomum*), *Chabertia ovina* (*Chabertia*), *Ancylostoma caninum* (*Ancylostoma*), *Uncinaria stenocephala* (*Uncinaria*), *Necator americanus* (*Necator*), *Bunostomum phlebotomum* (*Bunostomum*), *Dictyocaulus viviparus* (*Dictyocaulus*), *Metastrongylus elongatus* (*Metastrongylus*), *Filaroides hirthi* (*Filaroides*), *Aelurostrongylus abstrusus* (*Aelurostrongylus*), *Angiostrongylus cantonensis* (*Angiostrongylus*), *Syngamus trachea* (*Syngamus*), *Stephanurus dentatus* (*Stephanurus*), etc.), Rhabditida (for example, *Strongyloides stercoralis* (*Strongyloides*), *Micronema*, etc.), Spirurida (for example, *Thelazia rhodesi* (*Thelazia*), *Oxyspirura mansoni* (*Oxyspirura*), *Spirocerca lupi* (*Spirocerca*), *Gongylonema pulchrum* (*Gongylonema*), *Draschia megastoma* (*Draschia*), *Habronema microstoma* (*Habronema*), *Ascarops strongylina* (*Ascarops*), *Physaloptera praeputialis* (*Physaloptera*), *Gnathostoma spinigerum* (*Gnathostoma*), etc.), Filariida (for example, *Dirofilaria immitis* (*Dirofilaria*), *Setaria equina* (*Setaria*), *Dipetalonema*, *Parafilaria multipapillosa* (*Parafilaria*), *Onchocerca cervicalis* (*Onchocerca*), etc.), and Enoplida (for example, *Parafilaria bovicola* (*Parafilaria*), *Stephanofilaria okinawaensis* (*Stephanofilaria*), *Trichuris vulpis* (*Trichuris*), *Capillaria bovis* (*Capillaria*), *Trichosomoides crassicauda* (*Trichosomoides*), *Trichinella spiralis* (*Trichinella*), *Dioctophyma renale* (*Dioctophyma*), etc.); Trematoda, such as Fasciolata (for example, *Fasciola hepatica* (*Fasciola*), *Fasciolopsis buski* (*Fasciolopsis*), etc.), Paramphistomatidae (for example, *Homalogaster paloniae* (*Homalogaster*), etc.), Dicrocoelata (for example, *Eurytrema pancreaticum* (*Eurytrema*), *Dicrocoelium dendriticum* (*Dicrocoelium*), etc.), Diplostomata (for example, *Pharyngostomum cordatum* (*Pharyngostomum*), *Alaria*, etc.), Echinostomata (for example, *Echinostoma hortense* (*Echinostoma*), *Echinochasmus*, etc.), Troglotrematoidea (for example, lung flukes (*Paragonimus*), *Nanophyetus salmincola* (*Nancphy-* etus), etc.), Opisthorchiida (for example, *Clonorchis sinensis* (*Clonorchis*) etc.), Heterophyida (for example, *Heterophyes heterophyes* (*Heterophyes*), *Metagonimus vokogawai* (*Metagonimus*), etc.), Plagiorchiida (for example, *Prosthogonimus ovatus* (*Prosthogonimus*) etc.), and Schistosomatidae (for example, *Schistosoma japonicum* (*Schistosoma*) etc.); Cestoda, such as Pseudophylidea (for example, *Diphyllobothrium nihonkaiense* (*Diphyllobothrium*), *Spirometra erinacei* (*Spirometra*), etc.), and Cyclophyllidea (for example, *Anoplocephala perfoliata* (*Anoplocephala*), *Paranoplocephala mamillana* (*Paranoplocephala*), *Moniezia benedeni* (*Moniezia*), *Dipylidium caninum* (*Dipylidium*), *Mesocestoides lineatus* (*Mesocestoides*), *Taenia pisiformis* and *Taenia hydatigena* (*Taenia*), *Hydatigera taeniaeformis* (*Hydatigera*), *Multiceps multiceps* (*Multiceps*), *Echinococcus granulosus* (*Echinococcus*), *Echinococcus multilocularis* (*Echinococcus*), *Taenia solium* (*Taenia*), *Taeniarhynchus saginatus* (*Taeniarhynchus*), *Hymenolepis diminuta* (*Hymenolepis*), *Vampirolepis nana* (*Vampirolepis*), *Raillietina tetragona* (*Raillietina*), *Amoebotaenia sphenoides* (*Amoebotaenia*), etc.); Acanthocephala, such as *Macracanthorhynchus hirudinaceus* (*Macracanthorhynchus*) and *Moniliformis moniliformis* (*Moniliformis*); Linguatulida, such as *Linguatula serrata* (*Linguatula*); and other various parasites In different designations, examples of the helminths include, but are not limited to, Nematoda, such as Enoplida (for example, *Trichuris* spp., *Capillaria* spp., *Trichomosoides* spp., *Trichinella* spp., etc.), Rhabditia (for example, *Micronema* spp. *Strongyloides* spp., etc.), Strongylida (for example, *Strongylus* spp., *Triodontophorus* spp., *Oesophagodontus* spp., *Trichonema* spp., *Gyalocephalus* spp., *Cylindropharynx* spp., *Poteriostomum* spp., *Cyclococarcus* spp., *Cylicostephanus* spp., *Oesophagostomum* spp., *Chabestia* spp., *Stephanurus* spp., *Ancylostoma* spp., *Uncinaria* spp., *Bunostomum* spp., *Globocephalus* spp., *Syngamus* spp., *Cyathostoma* spp., *Metastrongylus* spp., *Dictyocaulus* spp., *Muellerius* spp., *Protostrongylus* spp., *Neostrongylus* spp., *Cystocaulus* spp., *Pneumostrongylus* spp., *Spicocaulus* spp., *Elaphostrongylus* spp., *Parelaphostrongylus* spp., *Crenosoma* spp., *Paracrencsoma* spp., *Angiostrongylus* spp., *Aelurostrongylus* spp., *Filaroides* spp., *Parafilaroides* spp., *Trichostrongylus* spp., *Haemonchus* spp., *Ostertagia* spp., *Marshallagia* spp., *Cooperia* spp., *Nematodirus* spp., *Hyostrongylus* spp., *Obeliscoides* spp., *Amidostomum* spp., *Ollulanus* spp., etc.), Oxyurida (for example, *Oxyuris* spp., *Enterobius* spp., *Passalurus* spp., *Syphacia* spp., *Aspiculuris* spp., *Heterakis* spp., etc.), *Ascaridia* (for example, *Ascaris* spp., *Toxascaris* spp., *Toxocara* spp., *Parascaris* spp., *Anisakis* spp., *Ascaridia* spp., etc.), Spirurida (for example, *Gnathostoma* spp., *Physaloptera* spp., *Thelazia* spp., *Gongylonema* spp., *Habronema* spp., *Parabronema* spp., *Draschia* spp., *Dracunculus* spp., etc.), and Filariida (for example, *Stephanofilaria* spp., *Parafilaria* spp., *Setaria* spp., *Loa* spp., *Dirofilaria* spp., *Litomosoides* spp., *Brugia* spp., *Wuchereria* spp., *Onchocerca* spp., etc.);

Acanthocephala (for example, *Filicollis* spp., *Moniliformis* spp., *Macracanthorhynchus* spp., *Prosthenorchis* spp., etc.); Trematoda including subclasses, such as Monogenea (for example, *Gyrodactylus* spp., *Dactylogyrus* spp., *Polystoma* spp., etc.) and Digenea (for example, *Diplostomum* spp., *Posthodiplostomum* spp., *Schistosoma* spp., *Trichobilharzia* spp., *Ornithbilharzia* spp., *Austrobilharzia* spp., *Gigantobilharzia* spp., *Leucochloridium* spp., *Brachylaima* spp., *Echinostoma* spp., *Echinoparyphium* spp., *Echinochasmus* spp., *Hypoderaeum* spp., *Fasciola* spp., *Fasciolides* spp., *Fasciolopsis* spp., *Cyclocoelum* spp., *Typhlocoelum* spp., *Paramphistomum* spp., *Calicophoron* spp., *Cotylophoron* spp., *Gigantcotyle* spp., *Fischoederius* spp., *Gastrothylacus* spp., *Notocotylus* spp., *Catatropis* spp., *Plagiorchis* spp., *Prosthogonimus* spp., *Dicrocoelium* spp., *Eurytrema* spp., *Troglotrema* spp., *Paragonimus* spp., *Collyriclum* spp., *Nanophyetus* spp., *Opisthorchis* spp., *Clonorchis* spp., *Metorchis* spp., *Heterophyes* spp., *Metagonimus* spp., etc.);

Cestoda, such as Pseudophyllidea (for example, *Diphyllobothrium* spp., *Spirometra* spp., *Schistocephalus* spp., *Ligula* spp., *Bothridium* spp., *Diplogonoporus* spp., etc.), and Cyclophyllidea (for example, *Mesocestoides* spp., *Anoplocephala* spp., *Paranoplocehala* spp., *Moniezia* spp., *Thysanosomsa* spp., *Thysaniezia* spp., *Avitellina* spp., *Stilesia* spp., *Cittotaenia* spp., *Andyra* spp., *Bertiella* spp., *Taenia* spp., *Echinococcus* spp., *Hydatigera* spp., *Davainea* spp., *Raillietina* spp., *Hymenolepis* spp., *Echinolepis* spp., *Echinocotyle* spp., *Diorchis* spp., *Dipylidium* spp., *Joyeuxiella* spp., *Diplopylidium* spp., etc.); and others including parasites belonging to Acanthocephala and Linguatulida.

The endoparasite control agent of the present invention is effective for controlling not only parasites that live in the body of an intermediate or final host, but also parasites that live in the body of a reservoir host. The compound represented by the general formula (I) of the present invention is effective for controlling parasites at their every developmental stage. For example, in the case of protozoa, the compound is effective against their cysts, precystic forms and trophozoites; schizonts and amoeboid forms at the asexual stage; gametocytes, gametes and zygotes at the sexual stage; sporozoites; etc. In the case of nematodes, the compound is effective against their eggs, larvae and adults. The compound of the present invention is capable of not only disinfecting parasites in the living body, but also even preventing parasitic infection by application to the environment as a route of infection. For example, soil-borne infection, i.e., infection from soil of crop fields and parks; percutaneous infection from water in rivers, lakes, marshes, paddy fields, etc.; oral infection from feces of animals such as dogs and cats; oral infection from saltwater fish, freshwater fish, crustaceans, shellfish, raw meat of domestic animals, etc.; infection from mosquitoes, gadflies, flies, cockroaches, mites and ticks, fleas, lice, assassin bugs, trombiculid mites, etc.; and the like can be prevented from occurring.

The endoparasite control agent of the present invention can be administered as a pharmaceutical for treatment or prevention of parasitosis in humans and animals of non-human mammalian or avian species. The mode of administration may be oral or parenteral administration. In the case of oral administration, the endoparasite control agent of the present, invention can be administered, for example, as a capsule, a tablet, a pill, a powder, a granule, a fine granule, a powder, a syrup, an enteric-coated preparation, a suspension or a paste, or after blended in a liquid drink or feed for animals. In the case of parenteral administration, the endoparasite control agent of the present invention can be administered, for example, as an injection, an infusion, a suppository, an emulsion, a suspension, a drop, an ointment, a cream, a solution, a lotion, a spray, an aerosol, a cataplasm or a tape, or in a dosage form which allows sustained mucosal or percutaneous absorption.

In the case where the endoparasite control agent of the present invention is used as a pharmaceutical for humans and animals of non-human mammalian or avian species, the optimum amount (effective amount) of the active ingredient varies with the purpose (treatment or prevention), the kind of infectious parasite, the type and severity of infection, the dosage form, etc., but in general, the oral daily dose is in the range of about 0.0001 to 10000 mg/kg body weight and the parenteral daily dose is in the range of about 0.0001 to 10000 mg/kg body weight. Such a dose may be given as a single dose or divided into multiple doses.

The concentration of the active ingredient in the endoparasite control agent of the present invention is generally about 0.001 to 100% by mass, preferably about 0.001 to 99% by mass, and more preferably about 0.005 to 20% by mass. The endoparasite control agent of the present invention may be a composition that can be directly administered, or a highly concentrated composition that needs to be diluted to a suitable concentration before use.

The endoparasite control agent of the present invention can be used in combination with any existing endoparasite control agent for the purpose of reinforcing or complementing its effect. In such a combined use, two or more active ingredients may be mixed and formulated into a single preparation before administration, or two or more different preparations may be administered separately.

EXAMPLES

Next, the present invention will be illustrated in detail by formulation examples and test example of the endoparasite control agent of the present invention, but the scope of the present invention is not limited by the following formulation examples and test example.

In Examples, "part" means a part by mass.

Formulation Example 1 (Emulsion)

Ten parts of a carboxamide derivative represented by the general formula (I) of the present invention, 6 parts of Sorpol 355S (surfactant, manufactured by Toho Chemical Industry), and 84 parts of Solvesso 150 (manufactured by Exxon) are uniformly mixed with stirring to give an emulsion.

Formulation Example 2 (Ointment)

One part of a carboxamide derivative represented by the general formula (I) of the present invention, 50 parts of white beeswax, and 49 parts of white petrolatum are well mixed to give an ointment.

Formulation Example 3 (Tablet)

Two parts of a carboxamide derivative represented by the general formula (I) of the present invention, 10 parts of vegetable oil (olive oil), 3 parts of crystalline cellulose, 20 parts of white carbon, and 65 parts of kaolin are well mixed and compressed into a tablet.

Formulation Example 4 (Injection)

Ten parts of a carboxamide derivative represented by the general formula (I) of the present invention, 10 parts of propylene glycol for use as a food additive, and 80 parts of vegetable oil (corn oil) are mixed to give an injection.

Formulation Example 5 (Solution)

Five parts of a carboxamide derivative represented by the general formula (I) of the present invention, 20 parts of a surfactant for ordinary use as a dissolution or suspension aid, and 75 parts of ion exchanged water are well mixed to give a solution.

Test Example

Test for Effect on Motion of Larvae of *Haemonchus* Nematode (*Haemonchus contortus*)

The compound of the present invention was prepared as solutions in 100% DMSO at the final concentrations of 50 ppm, 5 ppm, 0.5 ppm, 0.05 ppm and 0.005 ppm. DMSO stands for dimethyl sulfoxide.

A larval suspension containing 1st-stage larvae of *Haemonchus contortus* harvested by the Baermann technique (for example, see K. Nakazono et al., "Inclination of Baermann funnel wall and efficiency of nematode extraction" Proc. Assoc. Pl. Prot. Kyushu 33: 126-130 (1987)) was placed at a density of 20 larvae per well in a test plate, and 0.5 μL/well of the test solution containing the compound of the present invention diluted to a predetermined concentration was added to the test plate. The plate was kept under the conditions of 27° C./95% RH for 4 days. In the test, ivermectin was used for the positive control and DMSO was used for the negative control.

The motor ability of the larvae was examined with an automatic analyzer equipped with an LCD camera. The inhibitory effect on the motion of the larvae in each treatment plot was corrected based on the inhibitory effect in the plot treated with DMSO only for the negative control. The $EC_{50}$ value was calculated from the data on the corrected inhibitory effect on the motion of the larvae, and graded according to the criteria shown below.

The test was conducted in duplicate per plot.

Grading Criteria

| | |
|---|---|
| 0.05 ppm or less | A |
| 0.05 to 1 ppm | B |
| 1 to 10 ppm | C |
| 10 ppm or more | D |

As a result, the compounds 1-1, 1-2, 1-3, 1-4, 1-5, 1-6, 1-7, 1-8, 1-9, 1-10, 1-11, 1-13, 1-14, 1-15, 1-16, 1-17, 1-18, 1-19, 1-20, 1-21, 1-22, 1-23, 1-24, 1-25, 1-26, 1-27, 1-28, 1-29, 1-30, 1-31, 1-32, 1-34, 1-35, 1-36, 1-37, 1-38, 1-39, 1-40, 1-41, 1-42, 1-43, 1-44, 1-45, 1-46, 1-47, 1-48, 1-49, 1-50, 1-51, 1-52, 1-53, 1-54, 1-55, 1-56, 1-57, 1-58, 1-59, 1-60, 1-61, 1-62, 1-63, 1-64, 1-65, 1-66, 1-67, 2-1, 2-2, 2-3, 2-4 and 2-5 of the present invention showed the activity level graded as C or higher.

The results show that the compounds of the present invention are effective as an endoparasite control agent.

The invention claimed is:

1. A method for controlling an endoparasite, comprising orally or parenterally administering, to a mammal or a bird, an effective amount of an endoparasite control agent comprising, as an active ingredient, a carboxamide derivative represented by formula (I):

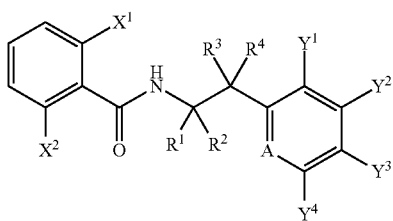

(I)

wherein
- A represents a C—$Y^5$ group (wherein $Y^5$ is a hydrogen atom or a ($C_1$-$C_6$) alkyl group),
- $X^1$ and $X^2$ may be the same or different, and each represent
- (a1) a hydrogen atom;
- (a2) a halogen atom;
- (a3) a ($C_1$-$C_6$) alkyl group;
- (a4) a halo ($C_1$-$C_6$) alkyl group;
- (a5) a ($C_1$-$C_6$) alkoxy group; or
- (a6) a halo ($C_1$-$C_6$) alkoxy group,
  - $R^1$ and $R^2$ may be the same or different, and are selected from the group consisting of
- (b1) a hydrogen atom;
- (b2) a halogen atom;
- (b3) a ($C_1$-$C_6$) alkyl group;
- (b4) a ($C_1$-$C_6$) alkoxy group; and
- (b5) a halo ($C_1$-$C_6$) alkyl group, or optionally
- (b6) $R^1$ and $R^2$ together with the carbon atom bound to $R^1$ and $R^2$ form a ($C_3$-$C_6$) cycloalkane,
  - $R^3$ and $R^4$ may be the same or different, and are selected from the group consisting of
- (c1) a hydrogen atom;
- (c2) a halogen atom;
- (c3) a ($C_1$-$C_6$) alkyl group;
- (c4) a ($C_1$-$C_6$) alkoxy group; and
- (c5) a halo ($C_1$-$C_6$) alkyl group; or optionally
- (c6) $R^3$ and $R^4$ together with the carbon atom bound to $R^3$ and $R^4$ form a ($C_3$-$C_6$) cycloalkane,
  - $Y^1$ represents
- (d1) a hydrogen atom;
- (d2) a halogen atom;
- (d3) a ($C_1$-$C_6$) alkyl group;
- (d4) a halo ($C_1$-$C_6$) alkyl group;
- (d5) a ($C_1$-$C_6$) alkoxy group; or
- (d6) a halo ($C_1$-$C_6$) alkoxy group,
  - $Y^2$ and $Y^4$ may be the same or different, and each represent
- (e1) a hydrogen atom;
- (e2) a halogen atom;
- (e3) a ($C_1$-$C_6$) alkyl group;
- (e4) a halo ($C_1$-$C_6$) alkyl group;
- (e5) a ($C_1$-$C_6$) alkoxy group; or
- (e6) a halo ($C_1$-$C_6$) alkoxy group, and
  - $Y^3$ represents
- (f9) a pyrimidyloxy group; or
- (f10) a pyrimidyloxy group having, on the ring, 1 to 3 substituting groups which may be the same or different and are selected from the group consisting of (a) a halogen atom, (b) a cyano group, (c) a nitro group, (d) a ($C_1$-$C_6$) alkyl group, (e) a halo ($C_1$-$C_6$) alkyl group and (g) a halo ($C_1$-$C_6$) alkoxy group, or a salt thereof.

2. The method according to claim 1, wherein the endoparasite control agent is orally or parenterally administered to a non-human mammal.

3. The method according to claim 2, wherein the non-human mammal is a domestic animal.

4. The method according to claim 1, wherein the mammal is a human.

5. The method according to claim 1, wherein the mammal is a non-human mammal.

6. The method according to claim 1, wherein
- $X^1$ and $X^2$ may be the same or different, and each represent
- (a1) a hydrogen atom;
- (a2) a halogen atom; or
- (a4) a halo ($C_1$-$C_6$) alkyl group,
  - $R^1$ and $R^2$ each represent (b1) a hydrogen atom,
  - $R^3$ and $R^4$ may be the same or different, and are selected from the group consisting of
- (c1) a hydrogen atom;
- (c3) a ($C_1$-$C_6$) alkyl group; and
- (c4) a ($C_1$-$C_6$) alkoxy group, or optionally
- (c6) $R^3$ and $R^4$ together with the carbon atom bound to $R^3$ and $R^4$ form a ($C_3$-$C_6$) cycloalkane,
  - $Y^1$ represents (d2) a halogen atom,
  - $Y^2$ and $Y^4$ each represent (e1) a hydrogen atom, and
  - $Y^3$ is
- (f10) a pyrimidyloxy group having, on the ring, 1 to 3 substituting groups which may be the same or different and are selected from the group consisting of (a) a halogen atom, (b) a cyano group, (c) a nitro group, (d) a ($C_1$-$C_6$) alkyl group, (e) a halo ($C_1$-$C_6$) alkyl group and (g) a halo ($C_1$-$C_6$) alkoxy group.

7. The method according to claim 1, wherein
- $X^1$ and $X^2$ may be the same or different, and are selected from the group consisting of
- (a1) a hydrogen atom;
- (a2) a halogen atom; and
- (a4) a halo ($C_1$-$C_6$) alkyl group,
  - $R^1$ and $R^2$ each represent (b1) a hydrogen atom,
  - $R^3$ and $R^4$ may be the same or different, and are selected from the group consisting of
- (c1) a hydrogen atom;
- (c3) a ($C_1$-$C_6$) alkyl group; and
- (c4) a ($C_1$-$C_6$) alkoxy group, or optionally
- (c6) $R^3$ and $R^4$ together with the carbon atom bound to $R^3$ and $R^4$ form a ($C_3$-$C_6$) cycloalkane,
  - $Y^1$ represents (d2) a halogen atom,
  - $Y^2$ and $Y^4$ each represent (e1) a hydrogen atom, and
  - $Y^3$ is
- (f10) a pyrimidyloxy group having, on the ring, 1 to 3 substituting groups which may be the same or different and are selected from the group consisting of (a) a halogen atom, (b) a cyano group, (c) a nitro group, (d) a ($C_1$-$C_6$) alkyl group, (e) a halo ($C_1$-$C_6$) alkyl group and (g) a halo ($C_1$-$C_6$) alkoxy group.

* * * * *